(12) United States Patent
Bothra et al.

(10) Patent No.: US 10,736,790 B2
(45) Date of Patent: Aug. 11, 2020

(54) ABSORBENT ARTICLE HAVING NATURAL FIBERS

(71) Applicant: Saathi, Inc., San Francisco, CA (US)

(72) Inventors: Tarun Bothra, Jodhpur (IN); Grace Kane, Delft (NL); Amrita Saigal, San Francisco, CA (US); Kristin Kagetsu, Ahmedabad (IN)

(73) Assignee: Saathi, Inc., San Francisco, CA (US)

( * ) Notice: Subject to any disclaimer, the term of this patent is extended or adjusted under 35 U.S.C. 154(b) by 591 days.

(21) Appl. No.: 15/358,362

(22) Filed: Nov. 22, 2016

(65) Prior Publication Data

US 2018/0140469 A1 May 24, 2018

(51) Int. Cl.
  *A61F 13/15* (2006.01)
  *A61F 13/53* (2006.01)
  *A61L 15/60* (2006.01)

(52) U.S. Cl.
  CPC ........ *A61F 13/15252* (2013.01); *A61F 13/53* (2013.01); *A61L 15/60* (2013.01); *A61F 2013/1526* (2013.01); *A61F 2013/530007* (2013.01); *A61F 2013/530481* (2013.01)

(58) Field of Classification Search
  CPC ........ A61F 13/15252; A61F 2013/1526; A61F 2013/530007; A61F 2013/530795
  See application file for complete search history.

(56) References Cited

U.S. PATENT DOCUMENTS

| | | | | |
|---|---|---|---|---|
| 3,110,609 A | * | 11/1963 | Bletzinger | ............... D04H 5/04 428/195.1 |
| 3,901,240 A | * | 8/1975 | Hoey | ................ A61F 13/00008 604/364 |
| 4,077,410 A | * | 3/1978 | Butterworth | ...... A61F 13/15203 602/45 |
| 4,300,981 A | | 11/1981 | Carstens | |
| 4,433,972 A | | 2/1984 | Malfitano | |
| 4,481,243 A | * | 11/1984 | Allen | ....................... B31F 1/07 428/154 |

(Continued)

FOREIGN PATENT DOCUMENTS

CN 104983517 A 10/2015
EP 2692319 A1 2/2014

(Continued)

OTHER PUBLICATIONS

Aakar Innovations PVT. Ltd, "completely Biodegradable and Compostable Absorbent Articles with Novel and Improved Absorbent Compositions," Form 2, Complete Specification, 1-16 (2016).

(Continued)

*Primary Examiner* — Susan S Su
(74) *Attorney, Agent, or Firm* — Foley Hoag LLP; Rajesh Vallabh

(57) ABSTRACT

Herein is disclosed a biodegradable absorbent article having a natural fiber cake which may include a mixture of plant fibers and plant pulp, such as from a banana plant, and in embodiments, includes an absorbent article having a permeable top sheet; a natural fiber cake that may be derived from plant material such as the banana plant; a water-insoluble back sheet; and an optional superabsorbent polymer, and wherein the absorbent article may be used for many purposes such as a sanitary napkin or urinary incontinence pads.

28 Claims, 3 Drawing Sheets

(56) References Cited

U.S. PATENT DOCUMENTS

| | | | |
|---|---|---|---|
| 5,185,009 A | 2/1993 | Sitnam | |
| 5,542,940 A | 8/1996 | Jonker | |
| 5,990,377 A * | 11/1999 | Chen | A61F 13/512 |
| | | | 442/79 |
| 6,642,428 B1 * | 11/2003 | Kurata | A61F 13/15203 |
| | | | 604/364 |
| 6,723,430 B2 * | 4/2004 | Kurata | A61F 13/15211 |
| | | | 428/378 |
| 8,969,652 B2 | 3/2015 | Bewick-Sonntag et al. | |
| 9,114,044 B2 | 8/2015 | Yoshiba | |
| 9,301,886 B2 | 4/2016 | Fernandez | |
| 9,365,972 B2 | 6/2016 | Scharpf et al. | |
| 2001/0014797 A1 * | 8/2001 | Suzuki | A61F 13/15211 |
| | | | 604/378 |
| 2001/0051796 A1 * | 12/2001 | Noda | A61F 13/15211 |
| | | | 604/383 |
| 2003/0135172 A1 * | 7/2003 | Whitmore | A61F 13/15658 |
| | | | 604/359 |
| 2003/0187414 A1 * | 10/2003 | Reiss | A61F 13/15211 |
| | | | 604/367 |
| 2006/0260773 A1 * | 11/2006 | Tan | D21C 9/004 |
| | | | 162/70 |
| 2008/0234645 A1 | 9/2008 | Dodge et al. | |
| 2009/0076472 A1 * | 3/2009 | Goldwasser | A61F 13/15658 |
| | | | 604/365 |
| 2011/0238026 A1 * | 9/2011 | Zhang | A61F 13/534 |
| | | | 604/372 |
| 2011/0319849 A1 * | 12/2011 | Collias | A61L 15/22 |
| | | | 604/372 |
| 2014/0343524 A1 * | 11/2014 | Tokita | A61F 13/53 |
| | | | 604/374 |

FOREIGN PATENT DOCUMENTS

| | | | | |
|---|---|---|---|---|
| EP | 2901992 A1 | 8/2015 | | |
| IN | 3129/MUM/2015 | 2/2017 | | |
| WO | WO-2013/146928 A1 | 10/2013 | | |
| WO | WO-2013146928 A1 * | 10/2013 | | A61F 13/49 |
| WO | WO-2015/186070 A1 | 12/2015 | | |

OTHER PUBLICATIONS

International Search Report and Written Opinion mailed in PCT Application No. PCT/US2017/062675.

Extended European Search Report for EP Application No. 17873145.1 dated May 29, 2020.

* cited by examiner

ABSORBENT ARTICLE HAVING NATURAL FIBERS

BACKGROUND

Disposable absorbent products are widely used in the medical field, for pets, and in any manner where a material for absorption of liquids and/or bodily fluids may be needed. Health and household items such as sanitary napkins, urinary incontinence pads, disposable diapers and the like typically have an absorbent core made from a chlorine bleached wood pulp that has been attached to a fluid containing plastic layer using an absorbent gel. The manufacture of these products requires cutting down entire trees and processing them to create the wood pulp used to create the absorbent layer, making the process very eco-unfriendly. The presence of the chlorine and gel prevents these products from being recycled. Instead they are typically disposed of in a landfill where it can take 500-800 years for them to degrade. Not only do the products take a long time to degrade, another problem results is the amount of trash that is accumulated from used pads, diapers and the like. In India, for example, pads create approximately 108,000 tons of waste annually. Most of this waste sits in landfills.

In Africa and India and many other places, women and girls have limited access to sanitary pads which can lead to an adverse effect on their education, productivity and health. In fact, millions of women and girls miss numerous days of school and/or work per year when they are menstruating. The same is true of women and men who have problems with urinary incontinence. Also, many brands of commercial sanitary pads are simply too expensive. For example, in India up to 88% of woman and girls miss school and/or work because of the lack of affordable sanitary pads. Some women even resort to use of rags and other materials that are not hygienic and can lead to infections. In addition, as stated above, conventional sanitary pads use bleach, chemical additives and other toxic materials that can be absorbed by the body, thereby adversely affecting the health of the user.

SUMMARY

Provided herein are absorbent articles and methods of making and using the absorbent articles. The absorbent articles comprise a natural fiber cake. Although the natural fiber cake may be formed from many types of natural fibers, desirably, the natural fiber is inexpensive, highly absorbent, non-toxic and fully compostable. The natural fiber may be a plant fiber. For example, banana tree bark takes approximately 2 to 5 years to degrade once the tree is cut down. Banana tree bark is also highly absorbent. Moreover, in certain parts of the world, the supply of banana tree bark is plentiful. Thus, in embodiments, the natural fiber cake comprises plant fibers derived from banana trees.

In one embodiment, a biodegradable and/or compostable absorbent article is provided comprising a natural fiber cake comprising a cellulosic material which includes a mixture of velutinous plant pulp and cellulosic fibers.

In another embodiment, an absorbent article is provided comprising a natural fiber cake comprising a cellulosic material which includes from about 60 to about 99 weight percent of plant pulp and from about 1 to about 40 weight percent of plant fibers having a length of from about 20 mm to about 100 mm.

In another embodiment, a biodegradable absorbent article is provided comprising a permeable top sheet; a natural fiber cake; a water-insoluble back sheet; and an optional super-absorbent polymer.

BRIEF DESCRIPTION OF THE DRAWINGS

Various embodiments of the present disclosure will be described herein below with reference to the figures wherein.

DESCRIPTION

Figure 1A:
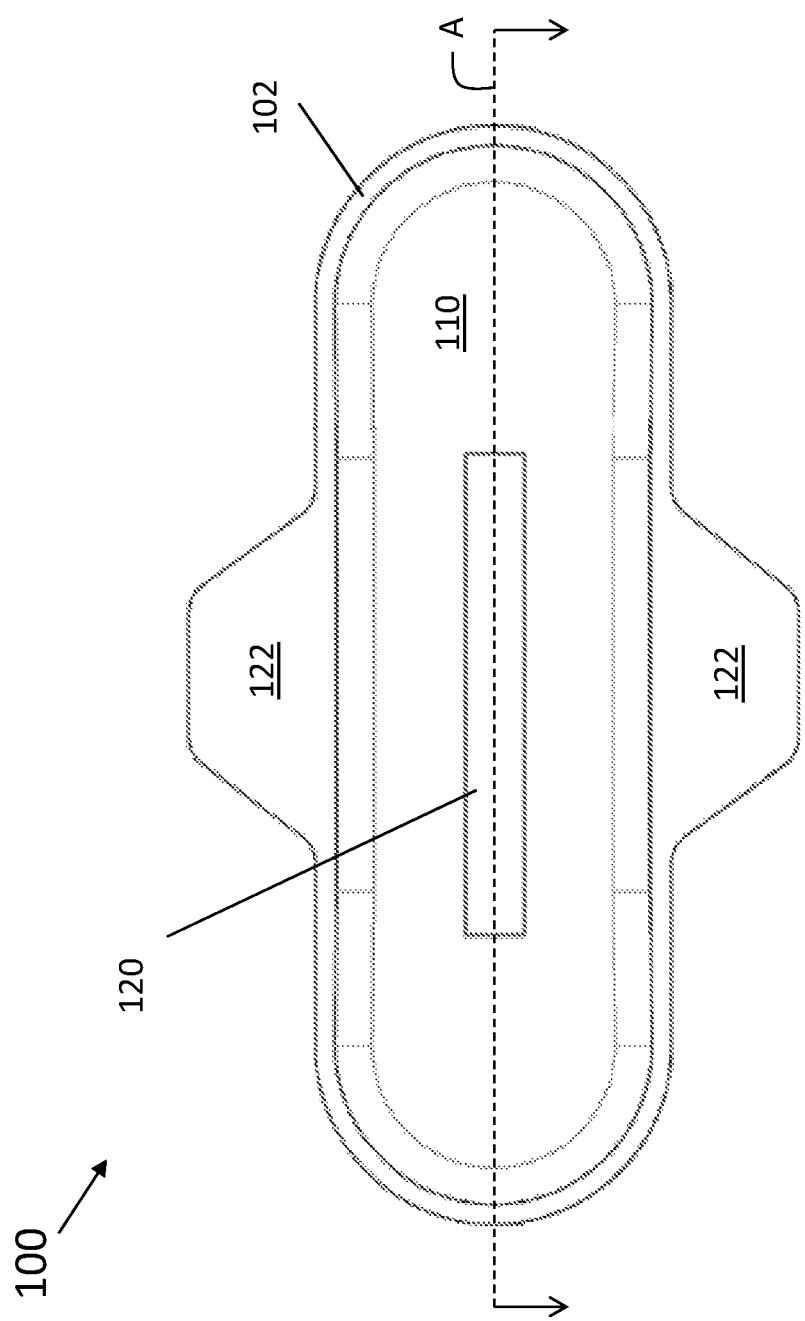
FIG. 1A shows a top view of an illustrative embodiment of an absorbent article configured to provide a sanitary napkin.

If not specifically stated herein, any percent or amount by weight is by weight of total solids or the specific layer, part, or material of article being described.

Definitions

The term "compostable" means any material that will decompose naturally as a result of the action of aerobic bacteria, fungi, and other organisms without leaving inorganic material in the soil.

The term "biodegradable" means capable of being destroyed and broken down into very small parts by natural processes, bacteria, fungi or other natural organisms or means.

The term "bio-based" material is a material intentionally made from or derived from substances derived from living (or once-living) organisms.

The term "velutinous" refers to having a soft, velvety surface such as that of certain plants or certain parts of plants or parts of plants following processing, including the wet pulping process described in the Examples, below.

The term "bodily fluids" refers to any fluid material naturally produced by animals including humans, and includes blood such as uterine blood, discharge, urine, saliva, puss, vomit, sweat, breast milk, defecation, and like bodily fluids.

The term "plant pulp" is defined herein as cellulosic plants which have at least 50% by weight of the lignin separated from the cellulose via thermal, chemical or mechanical processing, including the wet pulping process described in the Examples below.

Dimensions such as length, thickness, etc. may refer to an average value by which it is meant an average of the values from members of a population (e.g., average length determined from a population of fibers) or average of the values from multiple locations (e.g., average thickness determined from multiple locations across the surface of a layer). In other instances, a thickness may refer to a value determined at a particular location (e.g., the center of an absorbent article).

Use of directional terms, such as top, bottom, right, left, front, back, upper, lower, etc. are merely intended to facilitate reference to various surfaces that form components of the absorbent articles referenced herein and are not intended to be limiting in any manner.

Uses of Article

The absorbent article herein can be used to absorb most liquid materials, including water, and bodily fluids from humans and animals, including those as described above. The absorbent article can be formed into numerous products used in the capture and absorption of animal or human fluids including sanitary articles such as medical or surgical mats including auxiliary bedding sheets, auxiliary nursing-care mats, and the like; sheets, mats or pads for animals (pet pads); gauze pad or dressing; urinary incontinence napkin, pad, undergarment or pant; sanitary napkin or period pad; diaper for human or animal; breast or nursing pad; underarm pad; and the like. In embodiments, the absorbent article is configured to provide a sanitary napkin or period pad for absorbing blood. In embodiments, the absorbent article is configured to provide an incontinence pad for absorbing urine.

In embodiments, the absorbent article comprises a natural fiber cake positioned inside a pouch or envelope and/or positioned between two layers of sheets. In embodiments, the absorbent article comprises a back sheet and a top sheet and the fiber cake is positioned between the back sheet and the top sheet.

Figure 1B:
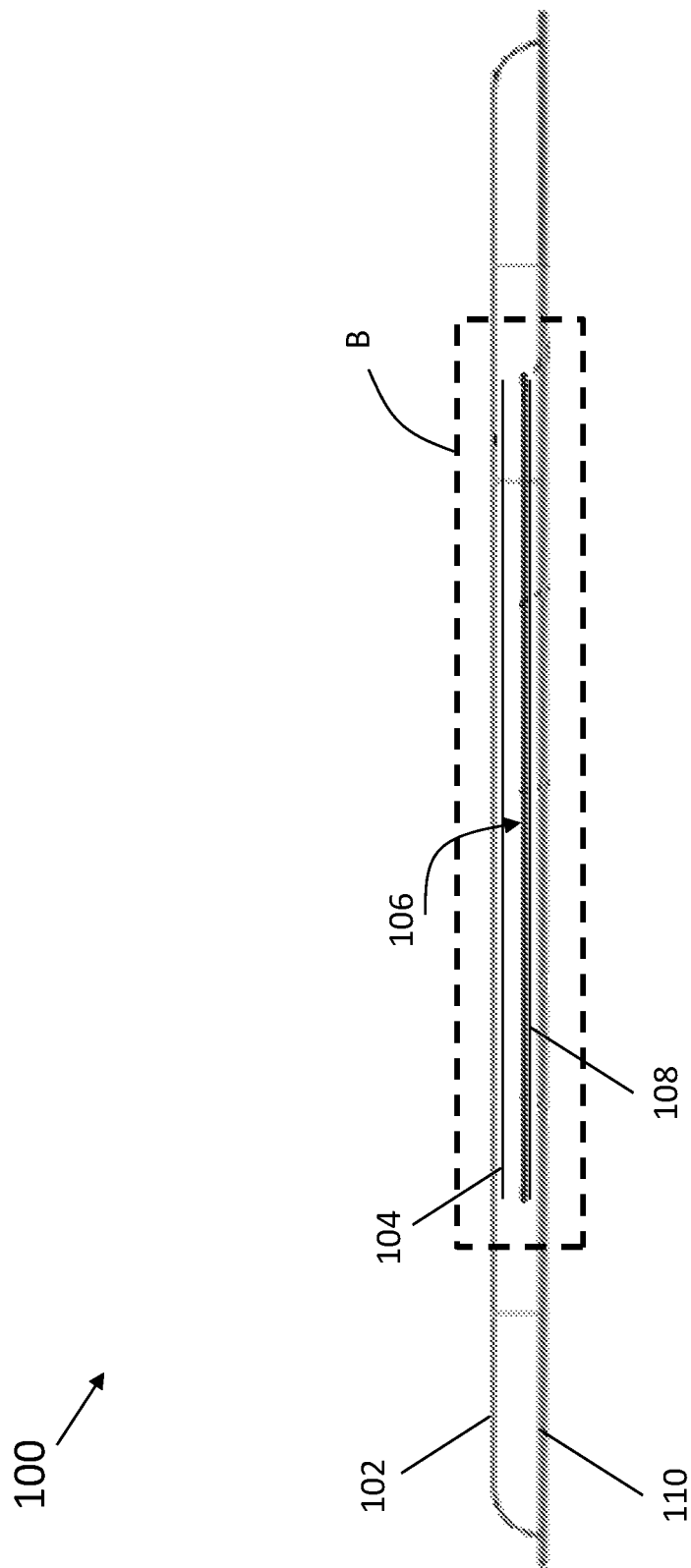
FIG. 1B shows a side, cross-sectional view of the absorbent article of FIG. 1A highlighting the central portion (dashed box) of the article.
Figure 1C:
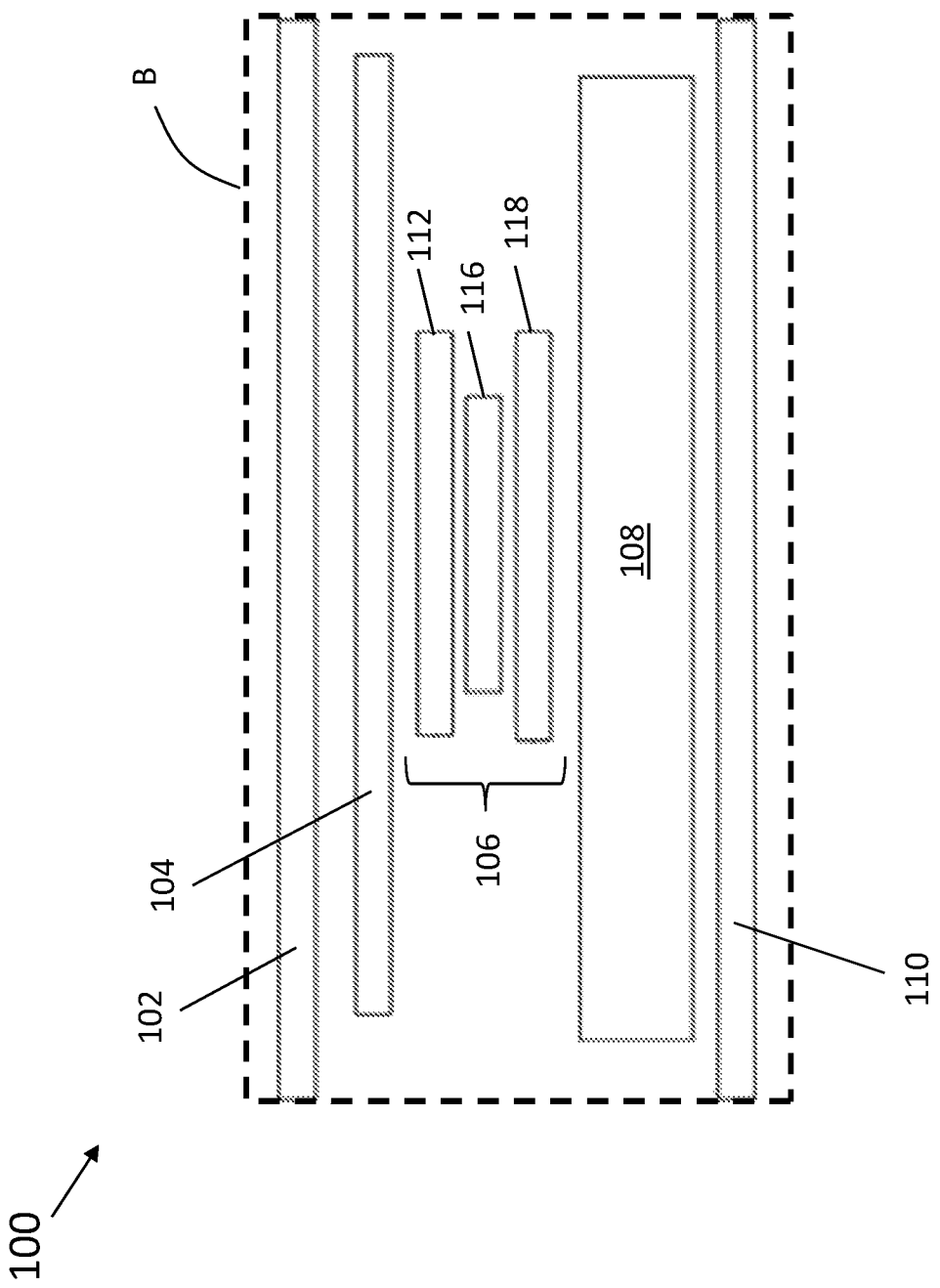
FIG. 1C shows an enlarged view of a portion of the absorbent article of FIG. 1B demonstrating the layered configuration.

FIGS. 1A-1C depict an illustrative absorbent article 100. FIG. 1A shows a top view of absorbent article 100 and depicts an embodiment in which the absorbent article 100 is configured to provide a sanitary napkin, period pad, or incontinence pad. FIG. 1B shows a side, cross-sectional view of absorbent article 100 taken along a section including axis A of FIG. 1A. FIG. 1C shows an enlarged view of a portion B of FIG. 1B.

As shown in FIG. 1C, the absorbent article 100 may comprise a top sheet 102, a layer 104 (e.g., a paper covering), a pouch 106 (which is optional), a natural fiber cake 108, and a back sheet 110. Pouch 106 may comprise an upper layer 112, a superabsorbent polymer (SAP) layer 116, and a lower layer 118. The paper covering 104 may be positioned in various locations within the absorbent article 100, e.g., between the back sheet 110 and the natural fiber cake 108, between the top sheet 102 and the pouch 106 as shown in FIG. 1C, or between the top sheet 102 and the natural fiber cake 108 (e.g., if the pouch 106 is not present).

Top Sheet

The top sheet 102 may comprise any material having properties including hydrophilic, permeable, soft, and flexible. In embodiments, the top sheet 102 is permeable, e.g., to blood and/or urine. In embodiments, the top sheet 102 is non-toxic and/or hypoallergenic. In embodiments, the top sheet 102 is perforated. In embodiments, the top sheet 102 is biodegradable and/or compostable. Examples of suitable materials for the top sheet 102 include plastics such as plastic films, and natural fibers. Suitable plastics include polyethylene, polypropylene, polyurethane, and the like; bio-based plastics including woven and nonwoven forms such as polyacetic acid, poly-3-hydroxybutyrate, and the like; fabrics such as nonwoven spun bounds (non-biodegradable), cotton spun lace nonwoven, jute or banana fiber spun lace nonwoven, polymer nonwoven, and combinations thereof. In embodiments, the top sheet 102 comprises nonwoven, spun bound polypropylene fabric (non-biodegradable); nonwoven cotton spun lace; nonwoven bio-based plastic; and like materials.

In embodiments, the top sheet 102 has a tensile strength of from about 25 to about 50, or from about 28 to about 45, or from about 34 to about 41 MPa in the Machine Direction (MD); from about 10 to about 40, or from about 13 to about 30, or from about 20 to about 24 MPa in the Cross Direction (CD); and from about 22 to about 27 N/5 cm (force per 5 cm tear length). The tensile strength can be measured using a tensile-testing machine with distance and load monitoring, such as 5942 Low-Range as manufactured by Instron. A sample may be inserted between the grips of the machine at a gauge length of 20 mm. The jaws were then pulled apart at a fixed rate of 20 mm/minute until sample failure. The load at sample failure is defined as the ultimate tensile strength.

In embodiments, the thickness of the top sheet 102 is from about 0.1 to about 1 mm, or from about 0.2 to about 0.7 mm or from about 0.3 to about 0.5 mm, or about 0.4 mm. In embodiments, the fluid penetration rate of the top sheet 102 is from about 98 to about 100 percent, or about 100 percent. In embodiments, the break elongation rate of the top sheet 102 is about 250 to about 500, or from about 300 to about 450 percent. In embodiments, from about 0.1 to about 1 grams/m$^2$, or from about 0.3 to about 0.5 grams/m$^2$ of nonwoven material is used as the top sheet 102. In embodiments wherein a superabsorbent pouch is used, the nonwoven material is used as the top sheet 102 in an amount of from about 0.01 to about 0.5 or from about 0.01 to about 0.1 grams.

Superabsorbent Polymer

Optionally, a superabsorbent polymer (SAP) is used to enhance the absorbency of the absorbent article 100 (e.g., in the form of a layer 116). A SAP may also be added to the natural fiber cake 108. Superabsorbent polymers are polymers that can absorb and retain extremely large amounts of a liquid relative to their own mass. SAPs can be biodegradable and non-biodegradable granular polymers or natural materials sometimes in the form of crystals or beads, that can absorb and retain from about 100 to about 500 times their weight of water or other liquids, or from about 10 to about 40 times their own weight of physiological saline or body fluids, and have excellent water retention. SAPs also have quick liquid absorption speed, high pressurized absorption, good gel strength, good moisture resistance and the like. In embodiments, SAPs can be low in monomer residue, nontoxic, odorless and non-stimulating to skin or hypoallergenic. Some SAPs are biodegradable into small molecules such as water, carbon dioxide and the like.

Properties of SAPs can include a saline water retention capacity of greater than about 35, or greater than about 40, or greater than about 45. Other properties include distilled water retention capacity of up to 300 as measured using the ratio of wet weight to dry weight after full saturation of the SAP.

Examples of suitable SAPs include low-density cross-linked SAPs and high-density cross-linked polymer materials such as acrylates and for example, sodium polyacrylate such as those from Arrochem in China; carboxy materials such as polycarboylate and for example MediSAP® from M$^2$ Polymer Technologies, and other polymers; natural materials such as bio-based SAPs including fly ash, sawdust, kiln dust, bio-based copolymers from various natural sources such as corn, algae, sugar cane, and the like; starch from various plant sources such as potatoes, yams, cassava, corn and the like, and for example ST-ARN from Qingdau, and the like, and combinations thereof. In embodiments, the SAP can include a mixture of polymer and bio-based materials. In specific embodiments, the SAP is a non-toxic, biodegradable mixture of polymer and starch such as Starch-g-poly (2-propenoic acid) sodium salt available from Maple Biotech. SAPs which comprise a component derived from a plant and are compostable are referred to throughout the present disclosure as "plant-derived compostable plastics." Starch-g-poly (2-propenoic acid) sodium salt is such an example.

In embodiments, the SAP is present in an amount of from about 0.1 to about 5, or from about 0.5 to about 3, or from about 1 to about 2 grams based on the weight of total solids.

Pouch

In embodiments, the SAP is layered inside the pouch 106 (see FIG. 1C). The pouch 106 may comprise the upper layer 112, the SAP layer 116 and the lower layer 118. The upper and lower layers 112, 118 may be formed of any of the materials listed above for the top sheet 102, including nonwoven materials and fabrics. In embodiments, the upper and lower layers 112, 118 of the pouch 106 may have a thickness of from about 0.05 to about 0.5 mm or from about 0.1 to about 0.2 mm. In embodiments, from about 0.01 to about 0.1 grams, or from about 0.03 to about 0.05 grams of nonwoven material is used in the pouch 106. The shape of the pouch 106 is not particularly limited. In embodiments, the pouch 106 has the shape of a rectangle. The length of the pouch 106 can be from about 100 to about 200 mm, or from about 120 to about 150 mm or about 140 mm, and the width can be from about 4 to about 30 mm, or from about 8 to about 20 mm, or about 15 mm.

Paper Covering

As shown in FIG. 1C, the absorbent article 100 may include the paper covering 104, which may be positioned between the pouch 106 and the top sheet 102. In embodiments, the paper covering 104 is biodegradable and/or compostable and may be recycled, bleached or unbleached. In embodiments, the paper covering 104 is from about 0.1 to about 5 mm, or from about 0.5 to about 3 mm, or from about 1 to about 2 mm thick. In embodiments, an amount of from about 0.1 to about 2 grams, or from about 0.5 to about 1 gram of paper is used.

Natural Fiber Cake

As shown in FIG. 1C, the absorbent article 100 further includes a natural fiber cake 108 between the top sheet 102 and the back sheet 110, with an optional SAP pouch 106 positioned above the natural fiber cake 108. Such configurations are suitable for use as a nursing pad, diaper, sanitary napkin, medical waste pad, urinary incontinence pad or pant or the like, and other articles useful in capturing and absorbing bodily fluids. If the absorbent article 100 is to be used as a gauze or medical pad, the top and/or back sheets 102, 110 are optional, as is the SAP layer 116 and pouch 106 that encloses the SAP layer 116.

The natural fiber cake 108 is defined herein as a mixture of natural fibers. In embodiments, the natural fiber mixture and/or the natural fiber cake 108 is biodegradable and/or compostable. Suitable materials for the natural fiber cake 108 include cellulosic material derived from plants. Plants include those selected from the group consisting of corn, abaca, wheat, barley, rice, hemp, sorghum, sugarcane, pineapple, kenaf, sisal, jute, banana, tea leaves, and the like, and combinations thereof. In embodiments, the plant is banana. The cellulosic material may be derived from banana fibers. The banana fibers may be from the stalk or stem (or pseudo-stem) of the banana plants. Banana stems/banana stem fibers are usually discarded after harvest of the bananas. Therefore, such banana stems/banana stem fibers are an excellent green source of material for the natural fiber cake 108 herein. Nothing has to be manufactured as a starting product, thereby making the product herein an eco-friendly product. Instead, a natural, organic waste product can be used as the starting point for the natural fiber cake 108 herein. Banana fibers comprise cellulose, hemicellulose, pectin and lignin.

Plant fibers such as banana stem fibers, have natural absorbency and high water retention properties and therefore, minimal processing is necessary. In addition, it may not be necessary to add products, especially harsh chemicals, to the natural fibers to increase absorbency. However, SAPs, such as natural, eco-friendly, SAPs may be added to increase absorbency.

The natural fiber cake 108 can be formed by cutting the plant fibers, followed by mixing and compressing the plant fibers and other desired components together to form a compacted cake having desired properties such as length and density. Cut fibers can be digested, softened, dried and fluffed to provide a material having desired absorbency, flexibility and softness.

In embodiments, the plant/plant component used to form the natural fiber cake 108 is chopped or cut into fibers having varying lengths. Banana fibers are robust and therefore, cutting and chopping the banana fibers does not affect the absorbent and water-retaining properties of the fibers. In embodiments, the plant fibers may be cut or chopped, and in embodiments, longitudinally, to have a length of individual fibers of from about 20 to about 100 mm, or from about 30 to about 75 mm, or from about 40 to about 65 mm, or from about 40 to about 55 mm, or from about 45 to about 50 mm.

In other embodiments, the plant/plant component used to form the natural fiber cake 108 may be subjected to a process to provide a pulp such as a velutinous pulp. The pulp may comprise fibers having a length of from about 1 to about 15 mm, or from about 2 to about 12 mm, or from about 3 to about 10 mm, or from about 5 to about 10 mm.

In embodiments, plant fibers are mixed with plant pulp to form the natural fiber cake 108. In embodiments, the natural fiber cake 108 includes from about 1 to about 40% or from about 10 to about 30%, or from about 15 to about 25% by weight of plant fibers based on the total weight of the natural fiber cake. In embodiments, the natural fiber cake 108 includes from about 60 to about 99%, or from about 70 to about 90% or from about 75 to about 85% by weight of pulp and in embodiments, velutinous pulp, based on the total weight of the natural fiber cake.

Using a mixture of plant fibers and plant pulp increases absorbency and water retention. Absorbency is a measurement relating to the amount of fluid that can be absorbed into a textile or fabric article in a specified amount of time or as a function of total weight or as a function of the area of the textile or fabric article. Absorbency is the ratio of the wet weight to dry weight of a sample of material saturated with liquid. The ability of a particular fabric or textile article to absorb a minimum quantity of fluid in a specified time frame or as a function of the base weight of the article is an important consideration. The natural fiber cake 108 may have an absorbency of from about 2 to about 14 g/g, or from about 4 to about 12 g/g, or from about 5 to about 10 g/g. These values may refer to the absorbency of water or blood. These values may refer to those as measured using the standard techniques described in the Examples, below.

In embodiments, the natural fiber cake 108 has a thickness of from about 2 mm to about 12 mm, or from about 4 mm to about 12 mm, or from about 8 mm to about 10 mm. The natural fiber cake 108, in embodiments, has a density of about 70 to about 200 kg/m$^3$, or from about 100 to about 175 kg/m$^3$ or from about 130 to about 150 kg/m$^3$. Density is a measurement of the number of fibers in a certain space. High density means a large number of fibers are packed together in a space, while a low density means a smaller number of fibers are contained in this same space. Density can be measured by known techniques such as liquid displacement, and the like.

In embodiments, the natural fiber cake 108 may further comprise a SAP, including any of the SAP described above. In this configuration, the pouch 106 may be absent. In other embodiments, the natural fiber cake 108 comprises a SAP in additional to the pouch 106 with the SAP layer 116.

In embodiments wherein the SAP is present only in the natural fiber cake 108 and there is no pouch 106, the SAP is used in an amount of from about 0.5 to about 4 grams, or from about 0.75 to about 2 grams, or from about 1 to about 2 grams by weight to total solids of the natural fiber cake. In embodiments including the pouch 106, the SAP may be present in the above amounts in the natural fiber cake 108 or in amounts of from about 0.1 to about 2 grams or from about 0.5 to about 2 grams.

Back Sheet

As shown in FIG. 1C, the absorbent article 100 may include the back sheet 110. The back sheet 110 may comprise any material capable of decreasing or preventing leaking of bodily fluids, such as those listed above, and in embodiments, blood, such as menstrual blood, urine or the like bodily fluids. The back sheet 110, in embodiments, has properties including being water insoluble, hydrophobic, flexible, non-permeable, softness, hypoallergenic, non-toxic, and the like. In embodiments, the back sheet 110 is water insoluble. In embodiments, the back sheet 110 is impenetrable to liquids, and in other embodiments, may be penetrable to air. In embodiments, the back sheet 110 may comprise a compostable and/or biodegradable material, such as a polymer and in embodiments, a bio-based polymer. Suitable materials for the back sheet 110 include plastic materials such as polyethylene, polypropylene, polyester, polyurethane such as polyurethane laminate (PUL), and for example, EcoPUL®, Amtrex® and the like; fabrics such as nylon, wool, cotton, banana-based fabric, and the like; and bio-based materials such as bio-based polyesters from sugar, starch and biogenic waste such as Maize-based bioplastic, and for example, Natur-Tec® BF703B, and the like.

In embodiments, the back sheet 110 has a tensile strength of from about 10 to about 40, or from about 15 to about 35, or from about 20 to about 30, or about 25 MPa. In embodiments, the back sheet 110 has a water vapor transmission of from about 250 to about 450, or from about 300 to about 410, or from about 350 to about 400, or about 370 g-mil/m$^2$/day. In embodiments, the thickness of the back sheet 110 is from about 0.1 to about 1 mm, or from about 0.2 to about 0.7 mm or from about 0.3 to about 0.5 mm, or about 0.4 mm. In embodiments, an amount of material for the back sheet 110 may be from about 0.1 to about 1 grams or from about 0.5 to about 0.8 grams.

In embodiments wherein the absorbent article 100 is in the form of a sanitary napkin, the back sheet 110 may comprise an adhesive layer 120 and optionally has a pull-strip covering the adhesive layer 120.

In embodiments wherein the absorbent article 100 is configured as a gauze pad or medical dressing, the back sheet 110 may comprise an absorbent material to allow for bodily fluids to enter into the natural fiber cake 108. Alternatively, the absorbent article 100 in the form of a gauze pad or medical dressing may comprise the natural fiber cake 108 positioned inside a pouch or envelope, or the natural fiber cake 108 positioned between two sheets, wherein said pouch or envelope or sheets have the properties and composition the same or similar to that of the top sheet 102 described herein.

The absorbent article can be formed into a sanitary napkin or urinary incontinence pad as depicted via absorbent article 100 of FIGS. 1A-1C and described above. As shown in FIG. 1A, on the opposite side of the back sheet 110, there may be the adhesive layer 120 covered with an adhesive strip covering or paper covering or the like functioning as a pull tab. The adhesive layer 120 may include any material capable of temporary bonding to an undergarment, for example, polyurethane adhesives, silicone adhesives, compostable pressure-sensitive adhesives such as bioTAK®, and the like. The absorbent article 100 may include wings 122 extending out the sides so as to cover the long edges of a panty as shown in FIG. 1A. A separate adhesive may be included on the opposite sides of the wings, along with an optional pull strip to allow for the wings to adhere to the opposite sides of the panty.

Such a sanitary napkin or incontinence pad may have dimensions including a width, not including the wings 122, of from about 40 to about 100 mm, of from about 50 to about 80 mm, or from about 60 to about 70 mm; a width including wings 122 of from about 100 to about 200 mm, or from about 120 to about 175 mm, or from about 125 to about 150 mm; and a length of the entire article of from about 100 to about 500 mm, or from about 200 to about 400 mm, or from about 250 to about 300 mm, or from about 250 to about 280 mm. The absorbent article 100 in the form of a sanitary napkin or urinary incontinence pad may have a thickness of the entire article of from about 1 to about 10 mm, or from about 3 to about 8 mm, or from about 4 to about 6 mm, or from about 5 to about 5.5 mm; and may have a weight of from about 3 to about 12 grams, or from about 5 to about 10 grams, or from about 7 to about 9 grams, and in embodiments, 8.75 grams.

In embodiments wherein the absorbent article 100 is in the form of a sanitary napkin or urinary incontinence pad, the plant fibers and plant pulp may be present in the natural fiber cake in an amount of from about 1 to about 25 grams, or from about 5 to about 20 grams, or from about 8 to about 15 grams, or from about 10 to about 12 grams.

In embodiments, an absorbent article consists of or consists essentially of a top sheet, a bottom sheet, a natural fiber cake, optionally, a paper covering and, optionally, a pouch. In embodiments, the natural fiber cake consists of or consists essentially of plant fibers, plant pulp, and optionally, a superabsorbent polymer. In embodiments, the pouch consists of or consists essentially of a superabsorbent polymer, an upper layer and a lower layer.

Process for Making Fiber Cake

U.S. Pat. No. 9,365,972, the content of which is hereby incorporated by reference in its entirety, discloses a process for producing a water-absorbent, high-porosity fibrous matrix from mechanically processed lignocellulose raw materials. The process describes mechanically processing a lignocellulose raw material with water, drying the wet mechanically processed material, and dry-fluffing the dried material by mechanical processing. In embodiments, the lignocellulose raw materials can be cut into fiber lengths of 0.1 to 3 cm prior to processing. The fiber material can be used in a water-absorbent and water-retentive pad.

Contrary to the disclosed process of the above-listed patent, in embodiments herein, the natural fiber cake 108 comprises a combination of cut fibers and fiber pulp. The fibers and fiber pulp may be derived from banana fibers. Herein, banana fiber can be harvested or purchased from known suppliers. The fibers are then cut into pieces of desired length (2-10 cm in embodiments) using a fiber cutter. A portion of the fibers is reserved and the other portion is subjected to a paper pulping process. In this process, the cut fibers are digested by cooking in a digester, softened mechanically and transformed into a pulp. The pulp is then spread into sheets and dried using accelerated drying at about 60° C. in a drying cabinet. The cut fibers and fiber pulp product are then mixed and fluffed by placing them together into a pulverizer where they are transformed into a fluff pulp.

The fiber mixture is then placed into molds by hand (or with the aid of machine) and compressed, e.g., using weights or a hydraulic pressure-assisted die.

The pouch 106 can be made by inserting SAP inside a small pouch of nonwoven fabric, for example. The same or similar material used as the top sheet 102 can be used to house the SAP. The pouch 106 may be sealed using known hand-operated heat sealer, or other known heat sealer. The pouch 106 can be filled with SAP using a manual-guided jig.

The absorbent article 100 may then be assembled by placing the natural fiber cake 108 on top of the back sheet 110 (or on top of a paper towel), the optional pouch 106 on the natural fiber cake 108, optional paper covering 104 or other paper product on top of the natural fiber cake 108 or the pouch 106 if present, and the top sheet 102 placed thereon. The absorbent article 100 may be sealed using a heated, pressurized stamp and then cut into the desired shape using a shape-cutting die.

Glue or other adhesive may be applied to an opposite side of the back sheet 110, e.g., using a manual silk-screening process, and non-stick paper applied to the top of the glue to form a protective covering.

The final product may then be sterilized according to regulations in a purpose-built UV cabinet.

Embodiments described herein are further illustrated in the following non-limiting examples.

EXAMPLES

Example 1

Natural Fiber Cake Preparation

A natural fiber cake was prepared as follows.

Raw banana stalks were separated and cut into sheets using a shredder.

The final product was banana fiber.

A smaller proportion of about 20% banana fiber was cut into short lengths (20-100 mm and in embodiments, 50 to 70 mm) using a paper shredding machine.

A larger proportion of about 80% of the banana fiber was subjected to a wet pulping process whereby the lignin and cellulosic material within the fibers were physically separated and a large proportion of the lignin was removed. The fiber was first immersed in water and subjected to heat and pressure in a digester. A mild alkali solution may be used as a softener. The digested pulp was then placed in a Hollander beater and subjected to wet mechanical processing. Water and other materials were removed by means of pressing the finished pulp by passing it through rollers or a pressurized stamp. The pulped fiber was dried into paper sheets or solid ingots.

To the approximately 80% banana pulp was added about 20% banana fiber and the combined material was place in a mechanical pulverizer and mixed together. In embodiments, an SAP (either Qingdao ST-ARN bio-based SAP or Starch-g-poly (2-propenoic acid) sodium salt) was added in an amount of approximately 1 g of SAP for every 10 g of fiber.

Portions of this combined fiber weighing approximately 12 g were separated and placed into dies to form predetermined piles. The separated material was then compressed into the shape of an absorbent article using a hydraulic press or other means thereby forming a compressed banana fiber cake.

Example 2

Preparation of SAP Pouch

In embodiments wherein an SAP pouch was used, a pouch having lower and upper nonwoven polypropylene layers was filled with starch-based SAP. In embodiments, a back glue such as a biodegradable pressure-sensitive adhesive such as BioTAK® S100, can be applied. In other embodiments, no glue was used and the pouch was placed on top of the fiber cake and the top and bottom sheets were then heat-sealed together and the pad was processed according to the below steps.

Example 3

Pad Processing

The pad cores were assembled by removing the compressed banana fiber cake from the mold and placing on top of an eco-friendly paper towel. The SAP pouch was then placed on top of the fiber cake. These pad cores were then sandwiched between a top sheet of a nonwoven polyethylene and a bottom sheet comprising bio-based polymer or bio-based plastic. Optionally, a glue such as a biodegradable pressure sensitive adhesive such as BioTAK S100, can be used around the edges for binding. In other embodiments, no glue is used and the top and bottom sheets were then heat-sealed together by means of a sealing board or a heat and pressure stamp.

The formed product was then cut into the desired shape of a sanitary napkin with a shaped cutting dye. After an adhesive was placed on the backside of the pads along with a non-stick paper covering over the adhesive, the products were then folded individually and sterilized using a UV cabinet, ready for packaging.

Example 4

Thickness Measurement

Prior to packaging, the thickness of the pad was measured using a pair of calipers such as a 0-150 mm caliper from Draper and other parameters were also measured. The measurements were found to be as follows:

| Pad Property | Pad Dimension |
| --- | --- |
| Central Thickness | 5.5 mm |
| Pad Length | 280 mm |
| Pad wing width | 150 mm |
| Pad core width | 70 mm |
| Total Pad Weight | 8.75 g |

Example 5

Absorbency Testing Using Water

In the experiments practiced herein, IS 5405:1980 can be used to specifically certify sanitary pads. This method has a binary (pass/fail) rate. The procedure is performed and if at the end of the procedure the pad does not leak, it has passed and can be certified for sale. More specifically, the base weight of the article is determined with the use of a top loading balance such as Precisa-IK-12000D-SCS as manufactured by Apex Scales. A bodily fluid or test fluid, deoxygenated goat's blood for example, is introduced in contact with the textile article and measured according to IS 5405: 1980.

Test fluid was prepared as follows. To 6 L of boiling water in a 10 L stainless steel or glass vessel, 4 grams of methyl paraben was added and stirred until dissolved. About 740 g of gum arabic or burn acacia was added and stirred until all the gum was dissolved. Water was added to make 8.05 L and the solution was allowed to stand for at least 24 hours. The liquid was then filtered through a later of glass wool. About 9 g of methylene blue, 1,470 ml of glycerin and 840 ml of water was added and stirred. The total volume was approximately 9.2 L. The solution was mixed thoroughly and allowed to stand at least 24 hours. The solution was shaken before use as testing fluid.

A sample of a sanitary pad in accordance with the specifications herein was place on a scale (Apex Scales 0.1 g rating, Precisa-IBK-120000D-SCS). The above testing fluid was then dripped at a rate of 15 ml/min from a pipette above the pad from a height of about 1 to about 2 mm. When the pad became saturated (i.e., no more water could be added without water dripping from the pad), the dry weight (weight before water added) and wet weight (weight at saturation) was measured. Absorbency was calculated as a ratio of the wet weight to the dry weight. The results showed an absorbency of 2 g/g to 10 g/g. The pad passed.

Absorbency Testing Using Blood

The above procedure was followed except that fresh goat's blood chilled to prevent coagulation was used before the blood was 2 hours old. After the napkin has absorbed the full amount of goat's blood, a standard weight of 1 kgf was placed for one minute on the portion of the sanitary napkin where the fluid was absorbed. The back and sides of the sanitary napkin were observed for any fluid showing up.

The thickness of the napkin was measured before absorbency testing with a pair of calipers such as a 0-150 mm caliper from Draper. The absorbency was measured at about 5 g/g. The napkin passed.

The claims, as originally presented and as they may be amended, encompass variations, alternatives, modifications, improvements, equivalents, and substantial equivalents of the embodiments and teachings disclosed herein, including those that are presently unforeseen or unappreciated, and that, for example, may arise from applicants/patentees and others.

What is claimed is:

1. A biodegradable absorbent article, comprising:
a natural fiber cake comprising a superabsorbent polymer and cellulosic material containing plant pulp and plant fibers, wherein the superabsorbent polymer comprises a plant-derived compostable material, wherein said plant fibers are derived from at least the banana plant, and the plant pulp comprises pulped plant fibers derived from at least the banana plant, wherein the natural fiber cake contains substantially no wood pulp;
a permeable top sheet covering one side of the natural fiber cake; and
a water-insoluble back sheet covering an opposite side of the natural fiber cake, wherein said water-insoluble back sheet comprises a bio-based material,
wherein the natural fiber cake, the permeable top sheet, and the water-insoluble back sheet are compostable.

2. The biodegradable absorbent article of claim 1, wherein said natural fiber cake comprises plant fibers derived from the banana plant and at least one plant selected from the group consisting of corn, abaca, wheat, barley, rice, hemp, sorghum, sugarcane, pineapple, kenaf, sisal, jute, tea leaves, and combinations thereof.

3. The biodegradable absorbent article of claim 1, wherein the permeable top sheet comprises a nonwoven material.

4. The biodegradable absorbent article of claim 1, wherein said superabsorbent polymer is mixed with said cellulosic material to form the natural fiber cake.

5. The biodegradable absorbent article of claim 1, wherein said natural fiber cake has an absorbency of from about 2 to about 14 g/g.

6. The biodegradable absorbent article of claim 1, wherein said natural fiber cake has a density up to about 200 kg/m$^3$.

7. The biodegradable absorbent article of claim 1, wherein said natural fiber cake comprises from about 60 to about 99 weight percent of plant pulp and up to about 40 weight percent of plant fibers.

8. The biodegradable absorbent article of claim 1, wherein the entire article is compostable.

9. The biodegradable absorbent article of claim 1, wherein the cellulosic material comprises a mixture of velutinous plant pulp and cellulosic fibers.

10. The biodegradable absorbent article of claim 1, wherein said cellulosic material comprises from about 60 to about 99 weight percent of cellulosic fibers.

11. The biodegradable absorbent article of claim 1, wherein the article comprises a sanitary napkin or a period pad.

12. The biodegradable absorbent article of claim 1, wherein the article comprises or is incorporated into a urinary incontinence napkin, pad, undergarment, or pant; a sanitary napkin or period pad; a medical or surgical mat; a bedding sheet; an auxiliary nursing-care mat; a sheet, mat, or pad for an animal; a gauze pad or dressing; a diaper for a human or an animal; a breast or nursing pad; or an underarm pad.

13. The biodegradable absorbent article of claim 7, wherein plant fibers have a length of from about 20 mm to about 100 mm.

14. The biodegradable absorbent article of claim 1, wherein the water-insoluble back sheet has an adhesive layer thereon configured to temporarily bond with an undergarment.

15. The biodegradable absorbent article of claim 1, wherein said permeable top sheet comprises a woven or nonwoven bio-based plastic, a nonwoven cotton spun lace, a non-woven jute spun lace, a non-woven banana fiber spun lace, or a combination thereof.

16. The biodegradable absorbent article of claim 15, wherein the nonwoven bio-based plastic comprises polyacetic acid or poly-3-hydroxybutyrate.

17. The biodegradable absorbent article of claim 1, wherein the superabsorbent polymer comprises a bio-based copolymer.

18. The biodegradable absorbent article of claim 17, wherein the bio-based copolymer is derived from corn, algae, sugar cane, potatoes, yams, or cassava.

19. The biodegradable absorbent article of claim 1, wherein the superabsorbent polymer comprises a non-toxic, biodegradable mixture of a polymer and starch.

20. The biodegradable absorbent article of claim 1, wherein the superabsorbent polymer comprises a Starch-g-poly (2-propenoic acid) sodium salt.

21. The biodegradable absorbent article of claim 1, wherein the cellulosic material in the natural fiber cake is derived from corn, abaca, wheat, barley, rice, hemp, sorghum, sugarcane, pineapple, kenaf, sisal, jute, banana, or tea leaves, or combinations thereof.

22. The biodegradable absorbent article of claim 1, wherein the bio-based material of the water-insoluble back sheet comprises bio-based polyesters derived from sugar or starch or biogenic waste.

23. The biodegradable absorbent article of claim 1, wherein the bio-based material of the water-insoluble back sheet comprises a Maize-based bioplastic.

24. The biodegradable absorbent article of claim 1, wherein the water-insoluble back sheet comprises nylon, wool, cotton, or a banana-based fabric.

25. A biodegradable absorbent article, comprising:
a natural fiber cake comprising a superabsorbent polymer and cellulosic material containing plant pulp and plant fibers, wherein the superabsorbent polymer comprises a plant-derived compostable material, wherein said plant fibers are derived from at least hemp, and the plant pulp comprises pulped plant fibers derived from at least hemp, wherein the natural fiber cake contains substantially no wood pulp;
a permeable top sheet covering one side of the natural fiber cake; and
a water-insoluble back sheet covering an opposite side of the natural fiber cake, wherein said water-insoluble back sheet comprises a bio-based material,
wherein the natural fiber cake, the permeable top sheet, and the water-insoluble back sheet are compostable.

26. The biodegradable absorbent article of claim 25, wherein said natural fiber cake comprises plant fibers derived from hemp and at least one plant selected from the group consisting of corn, abaca, wheat, barley, rice, sorghum, sugarcane, pineapple, sisal, jute, banana, tea leaves, and combinations thereof.

27. A biodegradable absorbent article, comprising:
a natural fiber cake comprising a superabsorbent polymer and cellulosic material containing plant pulp and plant fibers, wherein the superabsorbent polymer comprises a plant-derived compostable material, wherein said plant fibers are derived from at least kenaf, and the plant pulp comprises pulped plant fibers derived from at least kenaf, wherein the natural fiber cake contains substantially no wood pulp;
a permeable top sheet covering one side of the natural fiber cake; and
a water-insoluble back sheet covering an opposite side of the natural fiber cake, wherein said water-insoluble back sheet comprises a bio-based material,
wherein the natural fiber cake, the permeable top sheet, and the water-insoluble back sheet are compostable.

28. The biodegradable absorbent article of claim 27, wherein said natural fiber cake comprises plant fibers derived from kenaf and at least one plant selected from the group consisting of corn, abaca, wheat, barley, rice, hemp, sorghum, sugarcane, pineapple, sisal, jute, banana, tea leaves, and combinations thereof.

* * * * *